– – –

United States Patent [19]

Yamamoto et al.

[11] 4,252,788

[45] Feb. 24, 1981

[54] DENTAL COMPOSITION FOR PREVENTING AND INHIBITING DENTAL CARIES

[75] Inventors: Hiroji Yamamoto, Osaka; Hirohisa Okuda, Nara, both of Japan

[73] Assignee: Toyo Seiyaku Kasei Co., Ltd., Osaka, Japan

[21] Appl. No.: 39,178

[22] Filed: May 15, 1979

[51] Int. Cl.³ .................. A61K 7/16; A61K 7/18; A61K 7/22; A61K 33/24
[52] U.S. Cl. .................................. 424/52; 424/49; 424/54; 424/128; 424/131
[58] Field of Search .................. 424/49, 52, 128, 131, 424/54

[56] References Cited

PUBLICATIONS

Jenkins–Brit. Dent. J. 435–441 (1967).
Doss–J. Dent. Res 55(6), 1067–1075 (1976).
Drug Trade News–Jun. 11, 1962–pp. 48 & 50.
Chem. Abst. 71 29148(f) (1969)–Pappalaido et al.
Chem. Abst. 86 177,100(j) (1977)–Anan'er.
Hodjimarkos–Add. Bral. Biol., 3 253–293 (1968).

*Primary Examiner*—Douglas W. Robinson
*Attorney, Agent, or Firm*—Berman, Aisenberg & Platt

[57] ABSTRACT

A dental composition comprising about 0.1 to 5% by weight (as molybdenum) of a molybdate compound based on the total weight of the composition and a pharmaceutically acceptable carrier or diluent, prevents and inhibits dental caries. The composition exhibits its anticarious effect by inhibiting both digestion of the soft tissue in teeth with a protease and decalcification of the hard tissue in teeth with an acid.

8 Claims, No Drawings

DENTAL COMPOSITION FOR PREVENTING AND INHIBITING DENTAL CARIES

The present invention relates to a dental composition for preventing and inhibiting dental caries. More particularly, the dental composition of the present invention exhibits its anticarious effect by inhibiting both digestion of the soft tissue (organic components) in teeth with a protease and decalcification of the hard tissue (inorganic components) in teeth with an acid.

In order to prevent dental caries, there has been used a water-soluble fluoride, for example, sodium fluoride, stannous fluoride or sodium silicofluoride. These fluorides are usually formulated into a composition for applying onto the tooth surfaces, which is often carried out in a primary school, a kindergarten, a dental clinic and the like. Although the treatment obtains considerable results, the effect of the fluorides as a medicament is not always enough to prevent or inhibit dental caries.

The anticarious function or mechanism of the fluorides has been established by many studies. That is, fluoride ion ($F^-$) derived from the fluorides is reacted with hydroxyapatite of the hard tissue to provide acid resistance to the tissue and, thereby, makes the tissue more resistant against dissolution by an acid produced by oral bacteria (decalcification). Thus, the anticarious effect of the fluorides is exhibited by inhibiting the degradation of the hard tissue. The above treatment is, therefore, done with expectation of the action of $F^-$ derived from the fluorides on the hard tissue.

However, dental caries can not be fully illustrated merely by the degradation of the hard tissue. In addition to the hard tissue, there is present about 20% of protein as the soft tissue in dentin, most of which is collagen. Collagen is a stable protein and is not decomposed at the pH value of saliva in the mouth. Collagen is, however, decomposed by a specific protease, such as collagenase. Therefore, it is believed that dental caries occurs and advances as the result of not only the degradation of the hard tissue but also that of the soft tissue.

By this reason, as described above, the anticarious effect of the fluorides is insufficient since the effect merely depends upon the action of $F^-$ on the hard tissue and it is ineffective on the soft tissue.

Under these circumstances, we have intensively studied various medicaments having a significant effect for preventing and inhibiting dental caries and have found that certain molybdenum (VI) compounds impart soft-tissue resistance to protease digestion as well as increase hard-tissue resistance to acid dissolution.

One object of the present invention is to provide a dental composition for preventing dental caries. Another object of the present invention is to provide a dental composition for inhibiting advancement of dental caries. These and other objects and advantages of the present invention will be apparent from the following description.

The present invention provides a dental composition for preventing and inhibiting dental caries which comprises about 0.1 to 5% by weight (as molybdenum) of a molybdate compound based on the total weight of the composition and a pharmaceutically acceptable carrier or diluent. The dental composition of the present invention is applied to tooth surfaces and exhibits a superior anticarious effect by inhibiting both protease digestion of the soft tissue and acid decalcification of the hard tissue.

The molybdate compound to be used includes a dioxotetrafluoromolybdate of the formula $M_2MoO_2F_4$ wherein M is an alkali metal, such as lithium, sodium or potassium, or ammonium cation; an orthomolybdate of the formula $M_2MoO_4$ wherein M is as defined above; phosphomolybdic acid of the formula $P_2O_5 \cdot 24MoO_3$; and a phosphorus molybdate (dodecamolybdophosphate) of the formula $M_3(PO_4Mo_{12}O_{36})$ wherein M is as defined above. Examples of these molybdate compounds are sodium dioxotetrafluoromolybdate, potassium dioxotetrafluoromolybdate, ammonium dioxotetrafluoromolybdate, sodium orthomolybdate, potassium orthomolybdate, ammonium orthomolybdate, phosphomolybdic acid, sodium phosphorus molybdate and the like. In view of solubility of the compound and stability and application properties of the composition, a dioxotetrafluoromolybdate, particularly, sodium dioxotetrafluoromolybdate or ammonium dioxotetrafluoromolybdate is preferable. The molybdate compound is formulated into the composition in an amount of about 0.1 to 5% by weight (as molybdenum), preferably, about 0.5 to 5% by weight, more preferably, about 1 to 5% by weight, based on the total weight of the composition.

The pharmaceutically acceptable carrier or diluent to be used includes water, glycerin, propylene glycol, polyethylene glycol (macrogol), ethyl lactate or a mixture thereof and the like.

The dental composition of the present invention can be prepared in various forms, such as a solution, a suspension, or a paste (such as a macrogol ointment), for the local treatment of tooth surfaces. The dental composition can be prepared by conventional techniques involving procedures, such as mixing and dissolving the ingredients, as appropriate to the desired form of the composition. Optionally, the dental composition can contain another ingredient, such as a stabilizer, a preservative and the like. It is preferable to adjust the pH of the composition within the range of about 3 to 8 so as to improve the anticarious effect further.

In order to estimate the effect of the dental composition of the present invention, the following tests were conducted.

The ability to inhibit digestion of the soft tissue was estimated according to the method described in Yanagida et al, Shonishikagaku Zasshi, Vol. 9, page 39 (1971). That is, various molybdate compounds ($Na_2MoO_2F_4$, $K_2MoO_2F_4$, $(NH_4)_2MoO_2F_4$, $Na_2MoO_4$ or $K_2MoO_4$) were dissolved in deionized water in various concentrations to obtain various compositions to be tested. A certain amount of human decalcified dentin powder was treated with each of the above prepared compositions for certain minutes and then unbonded excess components were removed by dialysis to obtain a sample powder. Then, an opaque agar plate was prepared from a mixture of agar and the sample powder, and a protease (collagenase or trypsin) was added to the plate. The inhibiting ability was estimated by observing whether a clear zone was formed on the plate or not (the clear zone is formed by dissolution of the powder with the enzyme, and the formation thereof means digestion of the soft tissue). All the compositions tested showed a similar tendency regardless of the type of the molybdate compounds used.

The results are shown in Table 1.

TABLE 1

| Mo content in composition (%) | Ability to inhibit protease digestion | |
|---|---|---|
| | Composition of pH 3 | Composition of pH 5 |
| 5 | + | + |
| 1 | + | + |
| 0.5 | + | + |
| 0.3 | + | + |
| 0.1 | + | ± |
| 0.05 | ± | − |
| 0.01 | − | − |

Note
+ : Protease digestion is inhibited.
± : Protease digestion is faintly inhibited.
− : Protease digestion is not inhibited.

As is clear from Table 1, the dental composition inhibits protease digestion of the soft tissue at the molybdenum content of about 0.1 to 5% by weight. When molybdenum content is low, it is preferable to lower the pH of the composition. When sodium fluoride was used in the above test it showed no inhibition of protease digestion.

The ability to inhibit decalcification of the hard tissue was estimated according to the method described in Nishino. Osaka University Shigaku Zasshi, Vol. 14, page 1 (1969). That is, firstly, a certain amount of human dentin powder was treated with a composition (aqueous solution of a molybdate compound) to be tested for certain minutes and then unbonded excess components were removed by washing with water to obtain a sample powder. Then, the sample powder was treated with an acid solution (decalcification) and the amount of calcium in the solution, which was dissolved in the solution by action of the acid, was determined (sample calcium content). Similarly, untreated dentin powder was added to an acid solution and the amount of calcium in the acid solution was determined (control calcium content). From these values, a inhibition rate of decalcification was calculated as follows:

$$\text{Inhibition rate of decalcification} (\%) = \left(1 - \frac{\text{Sample calcium content}}{\text{Control calcium content}}\right) \times 100$$

The results are shown in Table 2. As a reference, a similar test was carried out using an aqueous solution containing 2% by weight of sodium fluoride. The results are also shown in Table 2.

TABLE 2

| Composition | | | Inhibition rate of decalcification (%) | | | |
|---|---|---|---|---|---|---|
| Molybdate compound | Mo (%) | pH | 0.5 hr decalcification | 1 hr decalcification | 3 hrs decalcification | 5 hrs decalcification |
| $Na_2MoO_2F_4$ | 1 | 3 | 63.30 | 64.65 | 66.67 | 66.28 |
| | 1 | 5 | 62.39 | 50.51 | 49.59 | 49.43 |
| $(NH_4)_2MoO_2F_4$ | 1 | 3 | 44.43 | 34.60 | 36.47 | 37.27 |
| | 1 | 5 | 44.43 | 45.45 | 42.39 | 43.12 |
| $Na_2MoO_4$ | 4 | 5 | 45.61 | 47.60 | 49.25 | 47.82 |
| | 4 | 7 | 44.04 | 42.17 | 33.80 | 35.42 |
| $K_2MoO_4$ | 4 | 3 | 30.80 | 33.33 | 35.42 | 34.52 |
| | 4 | 7 | 36.30 | 38.64 | 43.55 | 36.24 |
| $P_2O_5 \cdot 24MoO_3$ | 1 | 3 | 58.32 | 52.02 | 54.24 | 43.12 |
| | 4 | 7 | 45.22 | 44.82 | 47.39 | 44.61 |
| $Na_3PO_4 \cdot 12MoO_3$ | 1 | 3 | 42.20 | 42.42 | 41.11 | 40.94 |
| | 1 | 5 | 49.90 | 33.21 | 30.78 | 30.85 |
| Reference (NaF 2 %) | — | 5 | 43.91 | 40.66 | 47.97 | 38.76 |
| | — | 7 | 41.94 | 36.36 | 36.59 | 36.93 |

As is clear from Table 2, the dental composition of the present invention generally shows decalcification inhibitory effect equal to or higher than that of the composition containing NaF.

Further, the ability of the composition of the present invention to inhibit dental caries was tested in vivo as follows:

45 Male Sprague-Dawley rats (18 days old) were divided into three groups (15 rats/group). These rats were kept with the following cariogenic diet and deionized water during the test period (8 weeks).

CARIOGENIC DIET

| Ingredients | % by weight |
|---|---|
| Confectionary sugar | 64 |
| Casein | 15 |
| Palmitic acid | 10 |
| Choline chloride | 0.5 |
| Vitamines | 0.5 |
| Powdered whole milk | 5 |
| McCollum salt | 5 |

0.2 ml of a culture broth, which was prepared by anaerobic cultivation of *Streptococcus mutans* in brain-heart-infusion broth at 37° C. for 24 hours, was orally administered to each rat once a day for 5 days. On the first, 7th, 14th, 21st, 28th and 35th days of the test period, 10% solution of $(NH_4)_2MoO_2F_4$ in deionized water (pH 7.5) was applied twice to mandibular molar of each rat of the first group with a cotton applicator and dried for 5 minutes. Likewise, 2% solution of NaF in deionized water (pH 3.6) was applied to each rat of the second group. As a control, mere deionized water was also applied to each rat of the third group. After 8 weeks, rats were sacrificed and mandibula of each rat was isolated and autoclaved at 121° C. for 5 minutes to remove gingiva and the like attached thereto. After drying, the severity of dental caries of each isolated mandibular molar was estimated with a caries score according to the method described in P. H. Keyes, J. Dent. Res., 19, 1088–1099 (1958). The average caries score and inhibition rate of dental caries of each group are shown in Tables 3 and 4. In Tables 3 and 4, symbols of the severity of dental caries mean as follows:

Ds: slight dental caries (dental caries does not extend to a quarter part between enamel and dental pulp);

Dm: moderate dental caries (dental caries extends to a quarter to three quarters part between enamel and dental pulp); and Dx: extensive dental caries (dental caries extends to more than three quarters part between enamel and dental pulp).

The inhibition rate of dental caries is calculated as follows:

Inhibition rate of dental caries (%) =
$$\left(1 - \frac{\text{Average caries score of the group treated with the medicament}}{\text{Average caries score of the group treated with deionized water}}\right) \times 100$$

TABLE 3

| | Average caries score (± S.E.) | | |
|---|---|---|---|
| Severity | 1st group $(NH_4)_2MoO_2F_4$ | 2nd group NaF | 3rd group Deionized water |
| Ds | 3.9 ± 0.6 | 6.9 ± 0.8 | 8.6 ± 0.6 |
| Dm | 0.7 ± 0.2 | 2.3 ± 0.5 | 4.1 ± 0.9 |
| Dx | 0.2 ± 0.2 | 1.1 ± 0.4 | 3.2 ± 0.8 |

TABLE 4

| | Inhibition rate of dental caries (%) | |
|---|---|---|
| Severity | 1st group $(NH_4)_2MoO_2F_4$ | 2nd group NaF |
| Ds | 54.7 | 19.8 |
| Dm | 82.9 | 43.9 |
| Dx | 93.8 | 65.6 |

As is clear from Tables 3 and 4, the dental composition of the present invention containing $(NH_4)_2MoO_2F_4$ shows an excellent dental caries inhibitory effect. Particularly, as shown by the scores of Dm and Dx in Table 3, moderate and extensive dental caries are almost inhibited by the treatment with the composition. Moreover, the inhibition rate of dental caries is extremely superior to that of the composition containing NaF at any severity. Besides, during the test period, no side effect due to the medicaments used was observed and the rats treated with the medicament showed the similar weight gain to the rats of the control group (treated with deionized water).

Thus, the dental composition of the present invention inhibits both decalcification of the hard tissue and protease digestion of the soft tissue whereas NaF does not inhibit protease digestion of the soft tissue. Further, the dental composition of the present invention is useful from a viewpoint of toxicity since the molybdate compounds used in the present invention have toxicity as low as that of other medicaments commonly used for inhibition of dental caries. For example, testing $LD_{50}$ in mice, $(NH_4)_2MoO_2F_4$ shows $LD_{50}$(p.o.) of 124 mg/kg.

The dental composition of the present invention can be used by painting an appropriate amount thereof on tooth surface and maintaining it as it is for certain minutes. This treatment is repeated at regular intervals of time. For example, in case of using the liquid dental composition of the present invention for preventing dental caries, firstly, the tooth surface is thoroughly cleaned. Moisture is removed from the tooth to be treated and surrounding area and a tube may be inserted into the mouth to drain saliva when too much saliva is secreted, Then, the tooth surface is wiped with a swab, dried with an air blow gun and then rubbed with another swab soaked by the dental composition. The composition is applied to the tooth surface for 3 to 4 minutes at a time. In case of using the dental composition for inhibiting advancement of dental caries, firstly, softened dentin of the decayed part of the tooth is removed (using a spoon excavator), and the tooth surface is cleaned and dried. Then, the composition is applied to the tooth surface for 3 to 4 minutes as described above. These treatments are repeated several times every two to seven days. When the dental composition of low molybdenum content is used, it is preferable that the treatments are repeated more often.

As described hereinbefore, the dental composition of the present invention exhibits its anticarious effect not only by inhibiting decalcification of the hard tissue but also inhibiting protease digestion of the soft tissue.

The following examples illustrate the present invention but are not to be construed as limiting the scope thereof. In the examples, "part" is shown by weight.

EXAMPLE 1

Sodium dioxotetrafluoromolybdate monohydrate (11.2 parts) was dissolved in deionized water, pH thereof was adjusted to 3.0 with 30% NaOH, and the total amount of the resulting solution was made up to 100 parts with deionized water to obtain the desired liquid dental composition.

EXAMPLE 2

Ammonium dioxotetrafluoromolybdate (5.4 parts) was dissolved in deionized water, pH thereof was adjusted to 5.0 with conc. $NH_4OH$, and the total amount of the resulting solution was made up to 100 parts with deionized water to obtain the desired liquid dental composition.

EXAMPLE 3

Sodium orthomolybdate dihydrate (12.4 parts) was dissolved in deionized water, pH thereof was adjusted to 7.0 with 10% HCl, and the total amount of the resulting solution was made up to 100 parts with deionized water to obtain the desired liquid dental composition.

EXAMPLE 4

Sodium phosphorus molybdate decahydrate (7.2 parts) was dissolved in deionized water, pH thereof was adjusted to 5.0 with 30% NaOH, and the total amount of the resulting solution was made up to 100 parts with deionized water to obtain the desired liquid dental composition.

EXAMPLE 5

| Ingredients | Parts |
|---|---|
| Sodium dioxotetrafluoromolybdate monohydrate | 2.8 |
| Mixture of deionized water and glycerin (1 : 1) | 97.2 |

These ingredients were mixed and dissolved to obtain the desired liquid dental composition.

EXAMPLE 6

| Ingredients | Parts |
|---|---|
| Sodium dioxotetrafluoromolybdate monohydrate | 2.8 |
| 50% Lactic acid | 97.2 |

These ingredients were mixed and dissolved to obtain the desired liquid dental composition.

EXAMPLE 7

| Ingredients | Parts |
| --- | --- |
| Sodium orthomolybdate dihydrate | 2.5 |
| Mixture of deionized water and propylene glycol (1 : 1) | 97.5 |

These ingredients were mixed and dissolved to obtain the desired liquid dental composition.

EXAMPLE 8

| Ingredients | Parts |
| --- | --- |
| Sodium orthomolybdate dihydrate | 2.5 |
| Mixture of deionized water and macrogol 400 (1 : 1) | 97.5 |

These ingredients were mixed and dissolved to obtain the desired liquid dental composition.

EXAMPLE 9

| Ingredients | Parts |
| --- | --- |
| Potassium orthomolybdate pentahydrate | 3.5 |
| Mixture of deionized water and propylene glycol (1 : 1) | 96.5 |

These ingredients were mixed and dissolved to obtain the desired liquid dental composition.

EXAMPLE 10

| Ingredients | Parts |
| --- | --- |
| Sodium orthomolybdate dihydrate | 5.0 |
| Macrogol 400 | 49 |
| Macrogol 4000 | 49 |

Macrogol 4000 was added to macrogol 400 and dissolved by warming at 60° C. To the mixture was added sodium orthomolybdate dihydrate and solidified by cooling with stirring to obtain the desired paste dental composition.

What is claimed is:

1. A dental composition for preventing and inhibiting dental caries which comprises a pharmaceutically-acceptable carrier or diluent and from about 0.1 to 5 percent by weight as molybdenum and based on the total weight of the composition of a molybdate compound selected from the group consisting of an alkali-metal salt of dioxotetrafluoromolybdic acid and ammonium dioxotetrafluoromolybdate.

2. A dental composition according to claim 1, wherein said composition contains about 0.5 to 5% by weight as molybdenum of the molybdate compound.

3. A dental composition according to claim 1, wherein said composition contains about 1 to 5% by weight as molybdenum of the molybdate compound.

4. A dental composition according to claim 1, wherein the molybdate compound is a compound selected from the group consisting of sodium dioxotetrafluoromolybdate, potassium dioxotetrafluoromolybdate and ammonium dioxotetrafluoromolybdate.

5. A dental composition according to claim 4, wherein the molybdate compound is sodium dioxotetrafluoromolybdate or ammonium dioxotetrafluoromolybdate.

6. A dental composition according to claim 1, wherein the pH of the composition is within the range of about 3 to 8.

7. A dental composition according to claim 1 in the form of liquid.

8. A method for preventing and inhibiting dental caries which comprises applying to a tooth surface a dental composition according to claim 1.

* * * * *